(12) United States Patent
Yoshikawa et al.

(10) Patent No.: US 9,506,822 B2
(45) Date of Patent: Nov. 29, 2016

(54) DOUBLE-SIDE-COATED SURFACE STRESS SENSOR

(71) Applicant: NATIONAL INSTITUTE FOR MATERIALS SCIENCE, Ibaraki (JP)

(72) Inventors: Genki Yoshikawa, Ibaraki (JP);
Masakazu Aono, Ibaraki (JP);
Tomonobu Nakayama, Ibaraki (JP);
Frederic Loizeau, Neuchatel (CH);
Terunobu Akiyama, Neuchatel (CH);
Sebastian Gautsch, Neuchatel (CH);
Peter Vettiger, Neuchatel (CH)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 127 days.

(21) Appl. No.: 14/371,596

(22) PCT Filed: Apr. 17, 2013

(86) PCT No.: PCT/JP2013/061404
§ 371 (c)(1),
(2) Date: Jul. 10, 2014

(87) PCT Pub. No.: WO2013/157581
PCT Pub. Date: Oct. 24, 2013

(65) Prior Publication Data
US 2014/0352447 A1    Dec. 4, 2014

(30) Foreign Application Priority Data

Apr. 17, 2012 (JP) .................. 2012-094299

(51) Int. Cl.
*G01B 7/16* (2006.01)
*G01L 1/18* (2006.01)
*G01N 29/02* (2006.01)
*G01N 29/036* (2006.01)

(52) U.S. Cl.
CPC ............... *G01L 1/18* (2013.01); *G01L 1/183* (2013.01); *G01N 29/022* (2013.01); *G01N 29/036* (2013.01); *G01N 2291/0256* (2013.01); *G01N 2291/02827* (2013.01)

(58) Field of Classification Search
CPC .................................. G01L 1/18; G01B 7/16
USPC ........................................................ 73/774
See application file for complete search history.

(56) References Cited

U.S. PATENT DOCUMENTS

| 7,344,678 B2 * | 3/2008 | Majumdar ....... G01N 33/54373 204/403.01 |
| 2013/0133433 A1 | 5/2013 | Yoshikawa et al. |

FOREIGN PATENT DOCUMENTS

WO    2011/148774    12/2011

OTHER PUBLICATIONS

International Search Report issued Jun. 18, 2013 in corresponding International Application No. PCT/JP2013/061404.
Genki Yoshikawa et al., "Nanomechanical Membrane-type Surface Stress Sensor", Nano Letters 11, 2011, pp. 1044-1048.
H. P. Lang, "Nanomechanical Cantilever Array Sensors", Springer Handbook of Nanotechnology, B. Bhushan, Ed., 2007, pp. 443-459.
Alexander Bietsch et al., "Rapid functionalization of cantilever array sensors by inkjet printing", Nanotechnology 15, 2004, pp. 873-880.
P. A. Rasmussen et al., "Double sided surface stress cantilever sensor", Journal of Micromechanics and Microengineering 15, 2005, pp. 1088-1091.
Genki Yoshikawa et al., "Double-Sided-Coated Nanomechanical Membrane-Type Surface Stress Sensor (MSS) for One-Chip-One-Channel Setup", Langmuir, 2013, pp. 7551-7556.
* cited by examiner

*Primary Examiner* — Lisa Caputo
*Assistant Examiner* — Octavia Hollington
(74) *Attorney, Agent, or Firm* — Wenderoth, Lind & Ponack, L.L.P.

(57) ABSTRACT

A double-side-coated surface stress sensor includes a sensing membrane structure portion where at least two ends opposite each other are fixed on a mounting portion; a receptor layer that coats both surfaces of the sensing membrane structure portion; and an element detecting a stress, which is provided in the vicinity of at least one of the fixed two ends, opposite each other, of the sensing membrane structure portion or at least one of the fixed two ends, opposite each other, of the mounting portion, in which in a detection output is obtained from the element based on the stress which is applied onto the receptor layer coating both of the surfaces of the sensing membrane structure portion. Accordingly, it is possible to provide a double-side-coated surface stress sensor which coats both surfaces of the sensing membrane structure portion by the receptor layer, thereby obtaining a sufficiently large detection output.

16 Claims, 8 Drawing Sheets

STATIC MODE

DYNAMIC MODE

SINGLE-SIDE-COATED SURFACE→DEFORMATION

DOUBLE-SIDE-COATED SURFACE→EXPANSION

DOUBLE-SIDE-COATED SURFACE STRESS SENSOR

TECHNICAL FIELD

The present invention relates to a double-side-coated surface stress sensor which has high sensitivity by coating both surfaces of a sensing membrane structure portion of a surface stress sensor with receptor layers.

BACKGROUND ART

A sensor such as a nanomechanical sensor is well-known that includes a surface stress sensor (PTL 1, NPL 1) represented by a membrane-type surface stress sensor (MSS) and a cantilever sensor (NPL 2), and converts an item of target object into mechanical deformation or a stress of a sensing member so as to detect the obtained mechanical deformation or the stress by various means.

This type of sensor reads a surface stress or a change of weight induced by adsorbing a sample as deformation such as deflection and a change of resonant frequency respectively, to thereby detect the sample. The former is referred to as "static mode" and the latter is referred to as "dynamic mode". FIG. 1 is a diagram conceptually illustrating the static mode and the dynamic mode as an example of a cantilever sensor.

In the static mode, a receptor layer on which the sample is adsorbed has a single coated surface in common. This is in order for the cantilever sensor or the like to be efficiently deformed due to the surface stress applied by adsorbing the sample. FIG. 2 is a diagram illustrating structures of the cantilever sensor (a), a both ends fixed beam sensor (b), the membrane-type surface stress sensor (c) and operations thereof in the static mode. FIG. 2 illustrates structures (a) to (c) which are formed of a micromachinable single crystal silicon Si (100) having a high piezoresistance coefficient, and a detection output with shade (resistance change: $|\Delta R/R|$) obtained when the surface stress (3.0 N/m) is applied onto an area indicated by a light gray outline. In addition, FIG. 2 illustrates an enlarged top view of narrow portions in which piezoresistances are embedded.

Meanwhile, the above described "the piezoresistances are embedded" means piezoresistance portions are formed, and as described above, in a case where the sensor is formed of the single crystal silicon, a piezoresistive effect can be expressed on the aforementioned portion by doping an impurity such as boron only in a portion where the piezoresistance is to be formed. Such doping of the impurity can be realized by injecting ions on a required portion to be injected (specifically, a portion where stress is concentrated in FIG. 2) by an ion implantation method. The depth of ion injection is approximately 100 nm to 500 nm, and only the vicinity of a surface becomes the piezoresistance portion but the entirety does not become the piezoresistance in the depth direction. Meanwhile, as a matter of course, the piezoresistive effect cannot be expressed in a state where the ideal single crystal silicon has no carrier at all.

In a case of the single crystal silicon Si (100), since the detection output is given based on Expression of $\Delta R/R \propto (\sigma_x - \sigma_y)$, in order to obtain a large detection output, the stress ($\sigma_x \approx \sigma_y$, that is, $\Delta R/R \approx 0$) uniformly applied by the surface stress needs to be converted into uniaxial stress ($\sigma_x \gg \sigma_y$, or $\sigma_x \ll \sigma_y$, that is, $|\Delta R/R| \gg 0$) and amplified. In a common cantilever structure shown in FIG. 2(a), even though the width in the vicinity of the fixed end ("fixed portion" indicated by hatching) is made to be narrow, it is almost not possible to obtain the detection output ($\sigma_x \approx \sigma_y$). FIG. 2(b) illustrates a both ends fixed beam structure. This structure is configured to fix both ends of the beam to which the surface stress is applied and has a simple shape with a good symmetric property to be relatively easily formed, thereby obtaining high sensitivity. FIG. 2(c) illustrates a membrane-type surface stress sensor (MSS) structure. The surface stress applied onto a center film can be efficiently detected as the uniaxial stress in which each of four narrow peripheral portions having the piezoresistance is amplified (two of right and left narrow portions of piezoresistance in total: $\sigma_x \gg \sigma_y$, and two of upper and lower narrow portions of piezoresistance in total: $\sigma_y \gg \sigma_x$, both cases lead to $|\Delta R/R| \gg 0$). Accordingly, the highest sensitivity can be obtained. This structure has a highly symmetric property without free ends. Further, since four piezoresistances in total are connected with each other so as to form a full Wheatstone bridge (not illustrated), a stable operation is performed through self-compensation. In addition, in total of four piezoresistances in the upper, lower, right and left sides, the orientation of electric currents (for example, a [110] orientation of Si (100)) is aligned, and thus approximately four times output can be obtained.

Next, FIG. 3 conceptually illustrates a difference between deformations of a single-side-coated surface and a double-side-coated surface of the cantilever sensor which is operated in the static mode. In a case of the single-side-coated surface structure as shown in FIG. 3(a), the cantilever is deformed due to the surface stress on the single surface. Whereas, in a case of the double-side-coated surface structure as shown in FIG. 3(b), the surface stresses applied in both of the surfaces antagonize each other and thus the cantilever expands in a plane without being deflected. Therefore, since the cantilever is not substantially deformed, it is impossible to detect the sample based on the deformation. Particularly, when a detecting method of reading the cantilever sensor by means of optical methods such as a laser beam being employed in the static mode, it is impossible to detect the sample without deforming the cantilever in principle.

For this reason, the cantilever sensor has been required to employ "single-side-coated surface", and thus various surface coating methods have been developed. Among the methods, an ink jet spotting method can be exemplified as a representative method (NPL 3). This is a method of coating only a single-side surface with a receptor layer by dropping a small amount of a solution of a receptor onto the cantilever by using an ink jet method used in a printer or the like.

However, there are problems in this method in that an ink jet nozzle is unstable due to the concentration and viscosity of a solution, a coffee ring effect can be found when the dropped solution is dried, and thereby it is difficult to coat the receptor layer having high quality with satisfactory reproducibility. In addition, since a process of normally immersing a substrate for several to several tens of hours is included to form a self-assembled monolayer which is important as a method of functionalizing a surface, it is impossible to form the self-assembled monolayer having high quality by using the ink jet method.

When the detection output is obtained by coating both surfaces instead of coating the "single surface", it is possible to use, for example, a method of immersing all sensor elements in the solution of the receptor or a flow method of modifying a surface of sensor by allowing the solution of the receptor flow into the sensor element portion installed inside a sealed chamber. Accordingly, as long as a nanomechanical sensor of which both surfaces are coated with the receptor layer can be realized, it is possible to simply form the receptor layer having high quality with satisfactory reproducibility, which has been a problem of the nanomechanical sensor for a long time.

In an attempt to use the double-side-coated surface, the use of a piezoresistive cantilever has been reported (NPL 4). A sensor using the piezoresistance does not actually measure the "deflection" but a resistance change derived from the stress in accordance with the deformation such as the deflection. For this reason, in a case where both surfaces of the piezoresistance cantilever are coated by the receptor layer and the surface stress is applied to both of the surfaces, the stress generated by in-plane contraction/expansion is applied to the piezoresistance portion, and thus the detection output can be obtained.

However, in the cantilever structure, since the stress cannot be concentrated in the piezoresistance portion, the high sensitivity is not obtained. In addition, in a case where the single crystal Si(100) which has the high piezoresistance coefficient and can obtain the high sensitivity is used in a portion coated by the receptor layer or a portion, for example, where narrow regions are disposed in the vicinity of the aforementioned coated portion so as to concentrate the stress, there is a vital problem in that as illustrated in FIG. 2, the detection output can be rarely obtained by crystalline anisotropy in principle.

CITATION LIST

Patent Literature

PTL 1: WO 2011/148774 A1

Non Patent Literature

NPL 1: G. Yoshikawa, T. Akiyama, S. Gautsch, P. Vettiger, and H. Rohrer, "Nanomechanical Membrane-type Surface Stress Sensor," Nano Letters 11, 1044-1048 (2011).
NPL 2: H. P. Lang, "Nanomechanical Cantilever Array Sensors," In Springer Handbook of Nanotechnology, B. Bhushan, Ed. 2007; p. 443.
NPL 3: A. Bietsch, J. Y. Zhang, M. Hegner, H. P. Lang, and C. Gerber, "Rapid functionalization of cantilever array sensors by inkjet printing," Nanotechnology 15, 873-880 (2004).
NPL 4: P. A. Rasmussen, A. V. Grigorov, and A. Boisen, "Double sided surface stress cantilever sensor," Journal of Micromechanics and Microengineering 15, 1088-1091 (2005).

SUMMARY OF INVENTION

Technical Problem

The present invention has been accomplished in order to solve the problem in the related art and an object thereof is to provide a double-side-coated surface stress sensor which coats both surfaces of a sensing membrane structure portion with a receptor layer, thereby obtaining a sufficiently large detection output.

Solution to Problem

In order to solve the above described problem, the invention is configured as follows.

First, there is provided a double-side-coated surface stress sensor including a sensing membrane structure portion where at least two ends opposite each other are fixed on a mounting portion; a receptor layer that coats both surfaces of the sensing membrane structure portion; and an element detecting a stress, which is provided in the vicinity of at least one of the fixed two ends, opposite each other, of the sensing membrane structure portion or at least one of the fixed two ends, opposite each other, of the mounting portion, in which a detection output is obtained from the element based on the stress which is applied onto the receptor layer coating both of the surfaces of the sensing membrane structure portion.

Second, in the double-side-coated surface stress sensor according to the first invention, it is preferable that the stress applied onto the receptor layer be a stress generated by expanding and contracting the receptor layer.

Third, in the double-side-coated surface stress sensor according to the first invention, it is preferable that the stress applied onto the receptor layer be a stress excited by a magnetic field or radiation.

Fourth, in the double-side-coated surface stress sensor according to the second invention, it is preferable that the expansion and contraction of the membrane structure portion for detection be generated by adsorbing a substance to be detected onto the receptor layer.

Fifth, in the double-side-coated surface stress sensor according to the first to fourth inventions, it is preferable that the element include a piezoresistance.

Sixth, in the double-side-coated surface stress sensor according to the first to fifth inventions, it is preferable that the sensing membrane structure portion or the mounting portion be formed of a single crystal silicon, and the element be a region that is obtained by doping an impurity expressing an effect of the piezoresistance on a surface provided in the vicinity of at least one of the fixed two ends, opposite each other, of the sensing membrane structure portion or at least one of the fixed two ends, opposite each other, of the mounting portion.

Seventh, in the double-side-coated surface stress sensor according to the sixth invention, it is preferable that the doping of the impurity be performed by implanting or diffusing ions.

Eighth, in the double-side-coated surface stress sensor according to the first to seventh inventions, it is preferable that a portion where the element is provided in the end be a narrow portion formed into a small-width shape.

Ninth, in the double-side-coated surface stress sensor according to the first to seventh inventions, it is preferable that the ends fixed to the mounting portion include a first end and a second end on a first axis on a surface of the sensing membrane structure portion, and a third end and a fourth end on a second axis intersecting the first axis on the surface of the sensing membrane structure portion.

Tenth, in the double-side-coated surface stress sensor according to the ninth invention, it is preferable that the first axis and the second axis substantially intersect each other on the sensing membrane structure portion, and the sensing membrane structure portion be rotationally symmetric around an intersection point of the first axis and the second axis.

Eleventh, in the double-side-coated surface stress sensor according to the ninth or tenth invention, it is preferable that the narrow portion formed into a small width shape be provided in each of the first to fourth ends and the element be provided in each narrow portion which is provided in each of the first to fourth ends.

Twelfth, in the double-side-coated surface stress sensor according to the ninth or tenth invention, it is preferable that the element detecting the stress be provided in the vicinity of each of the first to fourth ends in the mounting portion.

Thirteenth, in the double-side-coated surface stress sensor according to the eighth invention, it is preferable that the ends be the first end and the second end on the axis in the longitudinal direction of the sensing membrane structure portion, the narrow portion be provided, which is formed into the small-width shape in at least one of the first end and the second end, and the element be provided in the narrow portion.

Fourteenth, in the double-side-coated surface stress sensor according to the first to thirteenth inventions, it is preferable that the receptor layer be formed of any one of a silane or Au-thiol self-assembled monolayer, a polymer, and an evaporated film.

Fifteenth, in the double-side-coated surface stress sensor according to the fourteenth, it is preferable that the receptor layer include at least one selected from a group formed of APTES, AEAPS, OTS, alkanethiol, MHA, single-strand oligo-DNA introducing a thiol group at the end, PSS, PMMA, and PEI.

Sixteenth, in the double-side-coated surface stress sensor according to the first to thirteenth inventions, it is preferable that the receptor layer be the surface of the sensing membrane structure portion.

Advantageous Effects of Invention

According to the double-side-coated surface stress sensor of the invention, it is possible to obtain the surface stress sensor in which both surfaces of the sensing membrane structure portion are coated by the receptor layer and which has sufficiently high sensitivity. In addition, since almost all of the materials can be used as the receptor layer, preparation conditions can be highly flexible. Further, it is possible to coat the surface of sensor by immersing an entire chip in a sample solution, and thus an application method can be simply preformed, which customizes a measuring system in accordance with a type or the number of the required sample by coating one chip with one type of the receptor layer, as "one chip—one channel".

DESCRIPTION OF EMBODIMENTS

A double-side-coated surface stress sensor according to the present invention is configured to comprise a sensing membrane structure portion (hereinafter, simply referred to as membrane portion) where at least two ends opposite each other are fixed on a mounting portion; a receptor layer formed on both surfaces of the membrane portion; and an element detecting a stress, which is provided in the vicinity of at least one of the fixed two ends, opposite each other, of the membrane portion or at least one of the fixed two ends, opposite each other, of the mounting portion.

Figure 1:
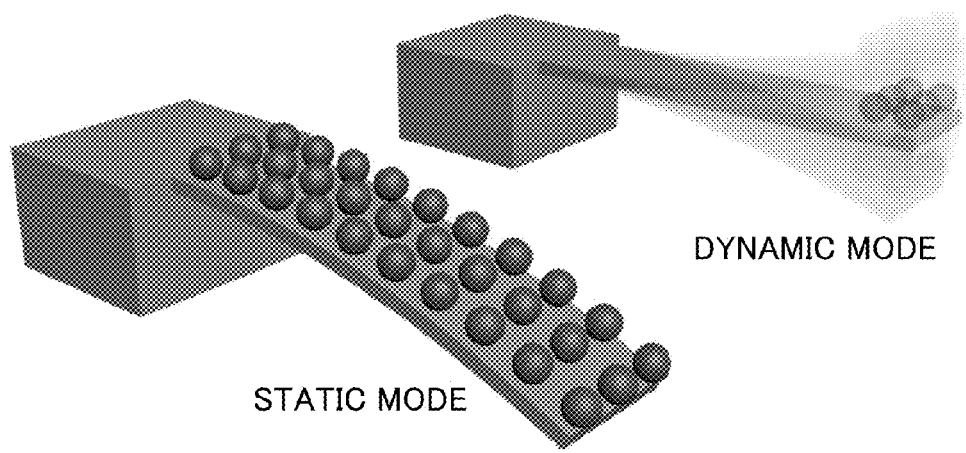
FIG. 1 is a diagram conceptually illustrating a static mode and a dynamic mode in a cantilever sensor.
Figure 2:
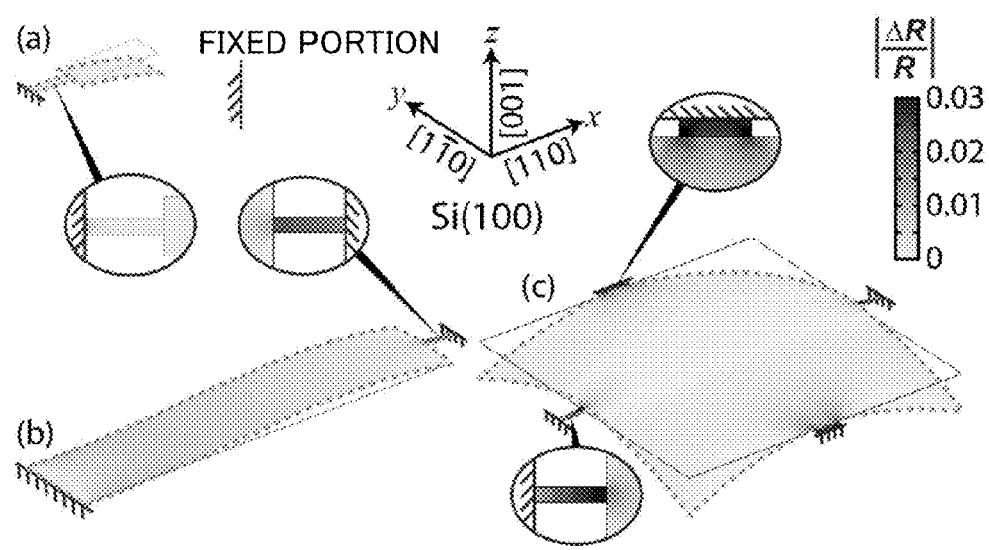
FIG. 2 is a diagram conceptually illustrating structures of the cantilever sensor and a surface stress sensor, and operations thereof.

It is possible to obtain high sensitivity when the above descried double-side-coated surface stress sensor of the invention is applied with respect to a membrane-type surface stress sensor (hereinafter, simply referred to as MSS) which has been recently developed as shown in FIG. 2(c) and then both surfaces are coated by the receptor layers (that is, a case where the stress is applied in both surfaces of a sensing member). This is because the stress is concentrated, on four beams which are detection portions of the piezoresistance being embedded, by in-plane expansion/contraction generated due to a surface stress applied in both surfaces of a silicon film.

Further, it is possible to efficiently obtain a detection output derived from the sample by disposing the above described four beams in consideration of crystallinity of the four beams. From the above, in a case where both surfaces are coated, even though the sensitivity is slightly decreased in comparison with a case where a single surface is coated, it is possible to realize high sensitivity. Due to the distinctive structure, the MSS has the sensitivity twenty times higher than the piezoresistance cantilever sensor, which is verified by an experiment and the finite element analysis, and has sensitivity equal to or higher than an optical read-out type sensor using a laser beam. For this reason, even in a case where both surfaces are coated, the measurement can be performed at least in one order or higher sensitivity than the piezoresistive cantilever sensor. In addition, further improvement of the sensitivity is expected by forming the receptor layer having high quality due to the double-side-coated surface.

Meanwhile, the stress concentration on the detection portion is caused by the sensing member to be deformed, and the sensing member is deformed by applying the stress onto the receptor layer thereof. The stress applied onto the receptor layer is excited by the existence of the substance to be detected in general.

Specifically, a mechanism in which the stress is applied to the receptor layer is as follows. The receptor layer is applied by not only physical contact such as a collision with or adsorption to the receptor layer of the substance to be detected but also by a remote force which is not accompanied with the physical contact such as a magnetic force generated by magnetic substances or radiation by radioactive substances. Alternatively, the receptor layer is applied by an indirect force generated by a chemical effect on the receptor layer due to a chain reaction of existing chemical substances including the substance to be detected in the measuring system.

When considering a process from the generation of the stress to the deformation of the sensing member from another point of view, there are two ways of applying the stress to the receptor layer.

(1) The expansion and contraction of the receptor layer is generated by supplying or stimulating a substance from the outside and thereby a stress occurs in the receptor layer itself. This case may occur when a polymer expands or contracts by absorbing molecules or when the chemical influence is exerted to the aforementioned receptor layer.

(2) A stress is generated from the outside of the receptor layer at first, and the generated stress is transferred to apply the receptor layer by some effects. This case corresponds to, for example, a case where molecules of a sample attached on the surface of the receptor layer generate a repulsive force or an attractive force to each other independently of a receptor, and such forces generated from the outside cause a sensing member to be deformed via the receptor layer. For example, it is not limited thereto, but when the receptor layer is very thin, which is a monomolecular layer, and samples adsorbed on the surface thereof do not enter into the receptor layer and thus a case where the samples directly interact with each other is likely to occur.

The present invention includes all of the modes described above.

Further, in the invention, it is also possible to use a portion of the sensing member, specifically, the surface thereof as the receptor layer instead of providing another receptor layer. For example, in a case where the sample is a substance (for example, a silane coupling agent in a case where the sensing member is silicon) which reacts with materials on both surfaces of the sensing member, it is possible to perform detection by directly exposing both of the surfaces to the sample to react with each other without coating the receptor layer on both of the surfaces of the sensing member.

Moreover, in the invention, when both of the surfaces of the sensing member are coated by the receptor layers, it is possible that a surface which is not coated by the receptor layer is not affected by non-specific adsorption of a substance other than the substance to be detected. In a case of the cantilever sensor which is required to perform the single-side-coated surface, since the surface which is not coated by the receptor layer is in a state where the sensing member such as silicon is exposed, there is a possibility of generating unintentional stress by physically adsorbing not only a substance such as the silane coupling agent as described above chemically reacting to the sensing member, but also the silicon surface. For this reason, there is a case where the surface which is not coated by the receptor layer is required to be coated by an inert layer formed of polyethylene glycol or the like. In contrast, in the invention, since both of the surfaces of sensing member are coated by the receptor layer, the unintentional stress by adsorbing the surface which is not coated by the receptor layer is not generated theoretically. Therefore, reliability of a signal detected by the sensor of which both surfaces are coated is higher than a single-side-coated sensor.

Hereinafter, the double-side-coated surface stress sensor of the invention will be described by exemplifying a case where the stress is generated by adsorbing the sample to be detected to the receptor layer; however, the invention is not limited thereto. Further, a term "adsorb" does not simply mean that the substance to be detected is physically adsorbed onto the receptor layer, but widely means that the substance to be detected includes even a chemical change of the receptor layer due to the chemical reaction caused in a measuring system.

Figure 3A:
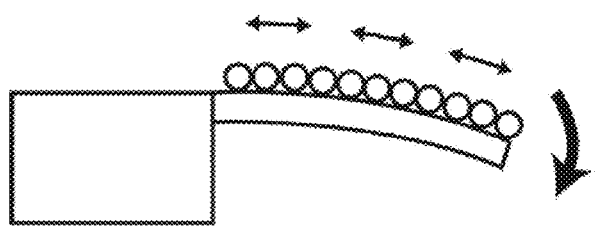
FIGS. 3(a) and 3(b) are diagrams conceptually illustrating different deformations between a case where a single surface is coated and a case where both surfaces are coated on the cantilever sensor which is operated in the static mode.
Figure 3B:
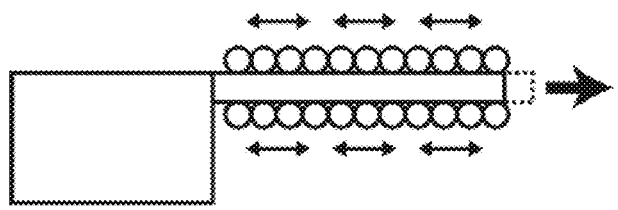

The invention is not limited to the MSS structure shown in FIG. 2(c) but may be a both ends fixed beam structure shown in FIG. 2(b). In the both ends fixed beam structure as shown in FIG. 2(b) and in the MSS structure shown in FIG. 2(c), both of the ends in the region where the length expands and contracts are fixed. That is, both of the ends of the beam in the longitudinal direction are fixed in the both ends fixed structure and both of the ends are fixed on each of two axes orthogonal to each other in the membrane portion in a square shape (or a circle) in the MSS structure. As described with reference to FIG. 3, the expansion is not easily detected due to the double-side-coated surface in the cantilever structure having one end as a free end, whereas in the two-end-fixed structure shown in FIGS. 2(b) and 2(c), the expansion (contraction depending on situation) due to the double-side-coated surface is regulated in both of the ends and thus a large stress generated by contraction or expansion is concentrated on the narrow portion of the end. Accordingly, it is possible to obtain a large detection output based on the above description.

Meanwhile, when the above described expansion occurs in a state where both ends are regulated, the membrane portion "escapes", that is, deforms upward or downward due to the sensor structure or asymmetry of both surfaces being coated in some cases. When such a deformation occurs, the obtained detection output in actual becomes the sum of "the stress derived from in-plane deformation (expansion and contraction)" and "the stress derived from deformation (deflection) orthogonal to a plane". Here, in a case of the MSS structure shown in FIG. 2(c), the detection output is obtained by configuring to have a bridge in the piezoresistance portion, whereas in cases where the membrane portion is deflected in a front direction and the membrane portion is deformed in a rear direction, reverse contribution to each other occurs as output signals generated from the bridge are referred to as plus (or minus) and minus (or plus). Therefore, it is necessary to confirm to which direction the membrane portion is deformed. The deformation direction can be estimated, for example, by measuring the absolute value of each piezoresistance in the bridge, but the estimation may be unreliable depending on situation in some cases.

Here, the above described problems can be resolved by using a structure having low sensitivity with respect to the deformation. For example, all narrow portions in the MSS structure can be removed. More specifically, such a property can be realized as below. In the structure shown in FIG. 4 described later, the narrow portion, that is, a piezoresistance beam, is removed, membrane portion in a round shape (silicon membrane portion) is directly connected to a bulk silicon substrate by using four points on the periphery thereof, and then the piezoresistance is disposed on the side of the bulk silicon of the connected portion. As a result of analysis obtained by the finite element method, in a case of this improved structure, since the membrane portion (silicon thin film portion) is pressed (or pulled) onto the bulk silicon, the stress derived from in-plane expansion and contraction is applied to the piezoresistance portion disposed on the bulk silicon. However, the stress derived from the deflection orthogonal to the plane of the membrane portion (silicon thin film portion) is not substantially applied to the piezoresistance portion since the deformation is not generated in the bulk silicon portion in the orthogonal direction.

Accordingly, since the detection output cannot be obtained by using this structure with the single-side-coated surface, a structure dedicated for double-side-coated surface can be obtained. In addition, there is an advantage in that rigidity of the chip is improved since the weakest narrow portion is removed in this structure. Further, needless to say, the material used in this improved MSS structure is not limited to the silicon similar to other structures.

In addition, the substance used in the receptor layer which coats both surfaces of the membrane portion can be used without specially limiting substances. That is, the receptor layer is formed any of the silane or Au-thiol self-assembled monolayer, the polymer, and the evaporated film regardless of a vapor phase, a liquid phase, and a solid phase.

Specifically, the silane-based materials are, for example, aminopropyl-triethoxysilane (APTES), N-(2-aminoethyl)-3-aminopropyltrimethoxysilane (AEAPS) and octadecyl-trichlorosilane (OTS). In addition, the thiol-based substances materials are, for example, alkanethiol, mercaptohexadecanoic acid (MHA), and single-strand oligo-DNA introducing a thiol group at the end. Further, poly(styrene sulfonate)(PSS), poly(methyl methacrylate) (PMMA), and poly(ethylene imine)(PEI) can be used as the polymer.

Further, as can be understood from that the double-side-coated surface stress sensor of the invention uses the expansion and contraction of the receptor layer which coats both surfaces of the membrane portion being a base material, it does not mean that the invention copes with the only stress in an ideal "surface" (namely, a plane having a thickness of zero). An analysis result of a sensor operation that the ideal surface stress is applied to both surfaces of the base material when the receptor layer is sufficiently thinner than the membrane portion of the base material, and an actual operation are coincide with each other with sufficiently high accuracy.

However, when a relatively thick polymer film or the like is used as the receptor layer, the analysis according to a surface stress model cannot correctly reflect the actual sensor operation and thus it is necessary to calculate the operation based on, for example, Timoshenko's bimetal theory. Even with the structure in which the thickness of the receptor layer compared with the membrane portion of the base material cannot neglect as described above, in terms of the structure for obtaining the detection output with high sensitivity through the expansion and contraction of the receptor layer which coats both surfaces of the base material, it is obvious that there is no essential difference compared with a case where the receptor layer is extremely thin as described with reference to FIG. 3. Accordingly, the surface stress sensor of the invention also includes the configuration to which the ideal surface stress model is not applied due to the thick receptor layer.

EXAMPLE

The aforementioned MSS will be exemplified as the surface stress sensor and an operation when both of the surfaces of the membrane portion of the MSS are coated by the receptor layer will be described below. However, this description is applicable to structures such as both ends fixed beam sensor other than MSS.

Figure 4:
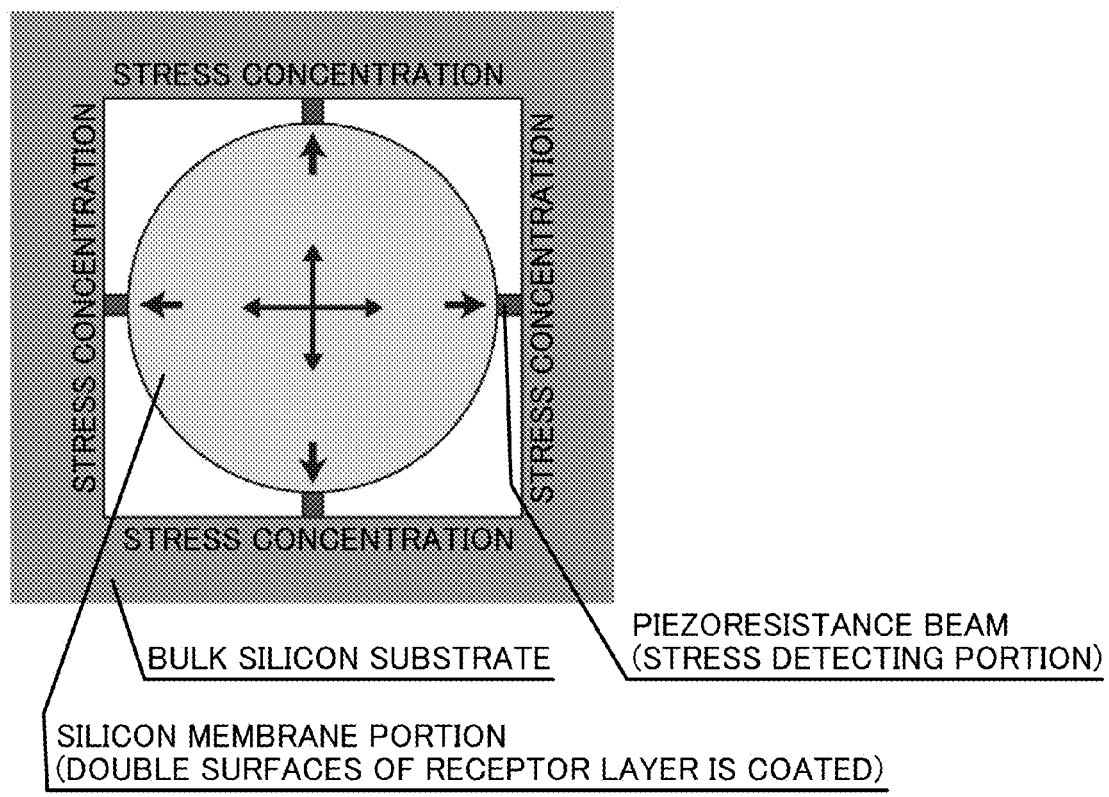
FIG. 4 is a top view illustrating a case where a sample is adsorbed on a sensing membrane structure portion (silicon thin film portion) of which both surfaces are coated and the surface stress is applied to both of the surfaces in an MSS.

FIG. 4 is a top view illustrating a case where the sample is adsorbed on the membrane portion (silicon thin film portion) of which both surfaces are coated and the surface stress is applied to both of the surfaces in the MSS. The membrane portion (silicon thin film portion) of which both surfaces are applied by the surface stress expands (or contracts) in a plane without being deformed. The membrane portion (silicon thin film portion) is connected to and supported by the bulk silicon substrate firmly supported by four narrow beams having the piezoresistance embedded therein. For this reason, when the membrane portion (silicon thin film portion) expands (or contracts) in the plane, the stress is concentrated on each of the four narrow beams. In this way, it is possible to efficiently read out the surface stress applied to both surfaces of the membrane portion (silicon thin film portion) by the piezoresistance embedded in each of the four narrow beams.

Figure 5B:
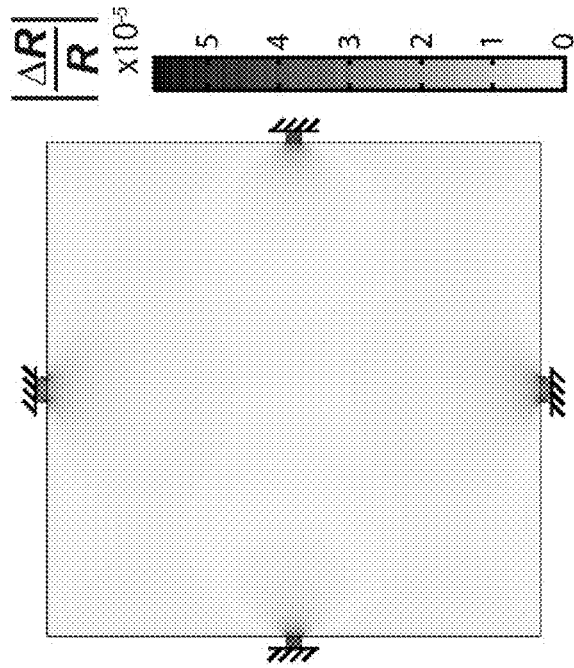
FIGS. 5(a) and 5(b) are diagrams illustrating a result of finite element analysis in a state where a stress is concentrated on a piezoresistance beam (stress detection portion) in the MSS.
Figure 5A:
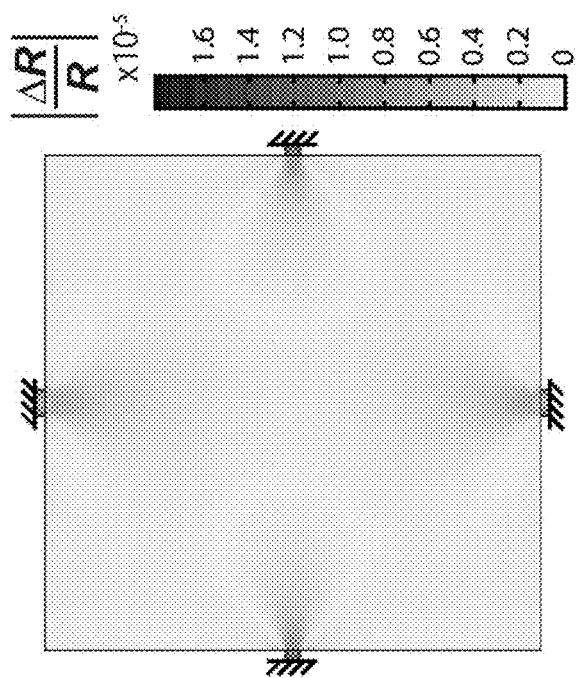
Figure 7:
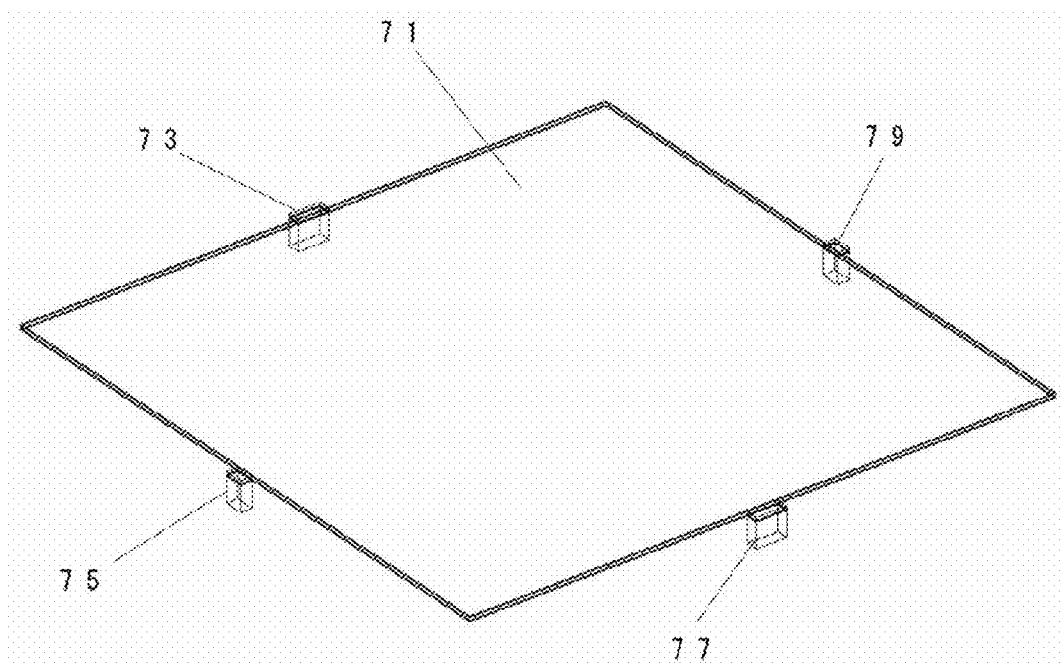
FIG. 7 is a perspective view conceptually illustrating an alternative MSS structure in which a location of the piezoresistance is changed.

FIG. 5 illustrates a result of finite element analysis. FIG. 5(a) is the MSS in a case of the double-side-coated surface, and FIG. 5(b) is the MSS in a case of single-side-coated surface. Meanwhile, in order to reduce the number of mesh at the time of calculation, the center of the membrane portion (silicon thin film portion) is not calculated as in the round shape but as in the square shape similar to FIG. 7 illustrating the model for the finite element analysis of the improved structure of MSS. As described above, the difference of the calculation result between in the round shape and the square shape is confirmed to be within a range of several % (NPL 1). Although the change of the piezoresistance ($\Delta R/R$) is plotted when the surface stress is uniformly applied to both surfaces (a) and the single surface (b) of the center of the membrane portion (silicon thin film portion), the stress is confirmed to be concentrated on each of the four narrow beams in both cases (a) and (b). Compared to the single-side-coated surface (b), the double-side-coated surface (a) has slightly wider stress distribution, but most of stress is still concentrated on each of the narrow beams and thus the reduction of sensitivity can be suppressed to be low.

Figure 6:
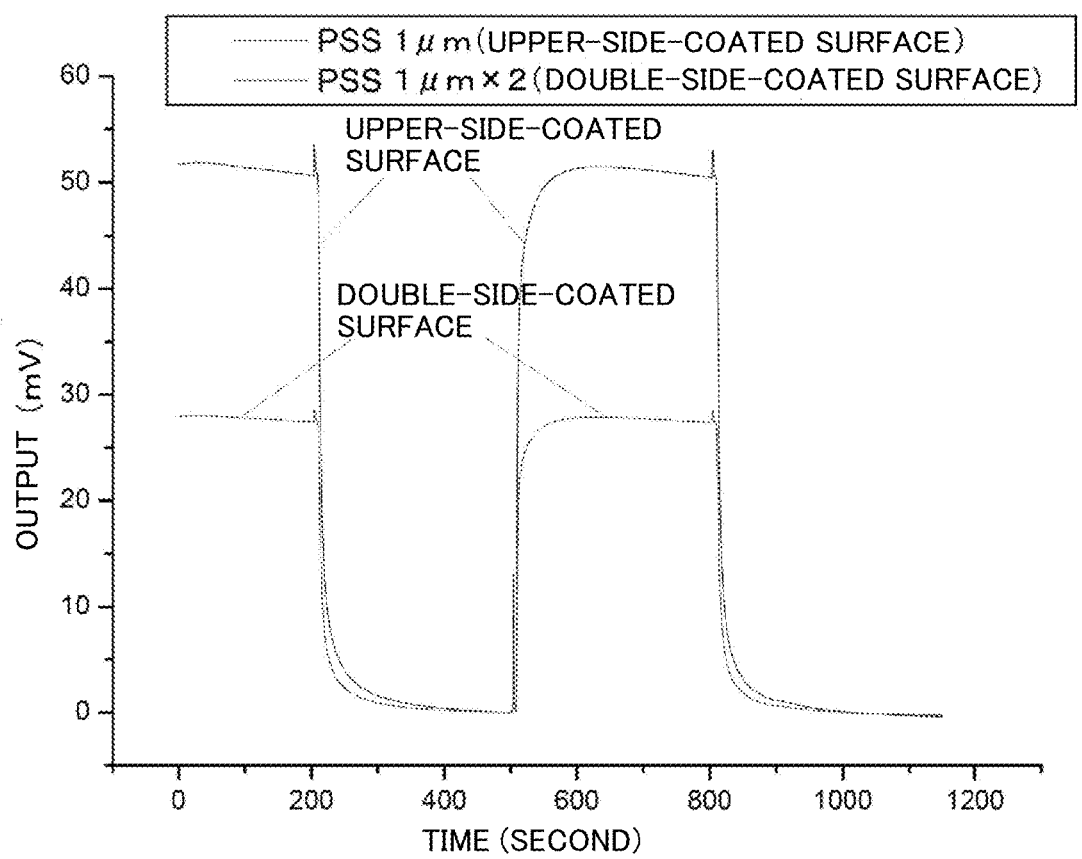
FIG. 6 is a graph illustrating an experiment result of measurement of a gaseous sample by coating a single surface and both surfaces of an MSS chip by the receptor layer.

FIG. 6 illustrates the experiment result of the measurement of a gaseous sample by coating a single surface and both surfaces of MSS chip. 1 μm of poly styrene sulfonate film is coated on the surface (in a case of double-side-coated surface, the upper surface and the lower surface each are coated by 1 μm of poly styrene sulfonate, that is, 2 μm in total) and 20% of vapor is measured. In a case of the double-side-coated surface, the detection output is slightly small similar to the result of finite element analysis, but it was verified to have one order or higher sensitivity than the piezoresistance cantilever sensor as yet.

FIG. 7 is a perspective view conceptually illustrating the MSS structure, for example, the improved structure, that is, a structure in which the membrane portion (silicon thin film portion) is directly connected to a frame-like portion, which is located around the narrow beams, thicker than the membrane portion (silicon thin film portion) without the narrow beams. In addition, FIG. 7 is a model view when the stress distribution in such an improved structure is analyzed by finite element method, and thus the silicon membrane portion 71 is in the square shape for the convenience of the calculation. However, as disclosed in NPL 1, it is understood that the difference of the calculation result between the silicon membrane portion 71 in the round shape and in the square shape is within a range of several %.

FIG. 7 illustrates a state where small cuboids 73, 75, 77, and 79 having a vertically long shape are respectively connected to the center of each side of the silicon membrane portion 71 which is in the square shape, but these indicate the vicinity of connection portions in the bulk silicon substrate directly connected with the silicon membrane portion 71.

The reason why the cuboids 73, 75, 77, and 79 have the vertically long shape is because the width of cuboids is significantly thicker than that of the silicon membrane portion 71. The thickness (length of the side that is parallel in the perpendicular direction to the film surface of silicon membrane portion 71) is calculated as 25 µm in the finite element analysis described later, but needless to say, as long as the thickness is not affected by the deflective deformation due to the stress, any thickness other than the aforementioned thickness may be accepted. In addition, the silicon membrane portion 71 is in the square shape in the example of FIG. 7, and in order to avoid contact of the periphery, contact portions as the cuboids 73, 75, 77, and 79 having wall thickness in the bulk silicon substrate protrude. However, in a case where the silicon membrane portion 71 is in the round shape or the like and can have a sufficient space from the periphery of the area except for the contact portions, a process of protrusion as described above is unnecessary. Alternatively, even though the silicon membrane portion 71 is in the square shape, it is unnecessary to provide these protruding portions in a case where a slightly narrow space may be made from the periphery.

Figure 8A:
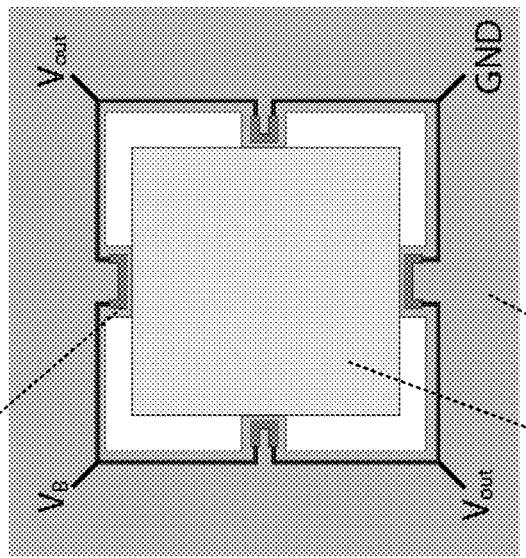
FIGS. 8(a) and 8(b) are top views conceptually illustrating the improved MSS structure as illustrated in FIG. 7 together with topology of the piezoresistance therein.
Figure 8B:
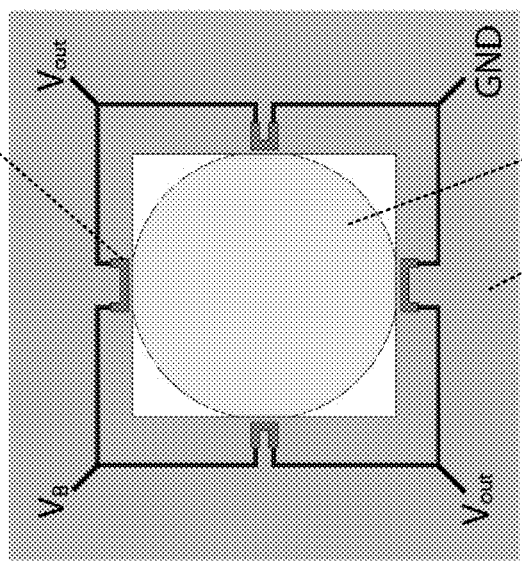

FIG. 8 conceptually illustrates the improved structure of MSS with the bridge formed by piezoresistance (stress detection portion) provided on the silicon substrate. FIG. 8(*a*) illustrates a case where the membrane portion is in the round shape and FIG. 8(*b*) illustrates a case where the membrane portion is in the square shape, but both cases are similarly operated. In FIG. 8, the detection output is obtained between a pair of residual terminals $V_{out}$-$V_{out}$ of the bridge by applying a voltage between a terminal $V_B$ and a terminal GND. In addition, each of the four piezoresistances in FIG. 8 is generated by doping impurities appropriate for ion implantation or the like in the vicinity of the connection portions, which are connected to the silicon membrane portion 71 of upper surfaces of the cuboids 73, 75, 77, and 79 in FIG. 7.

Figure 9A:
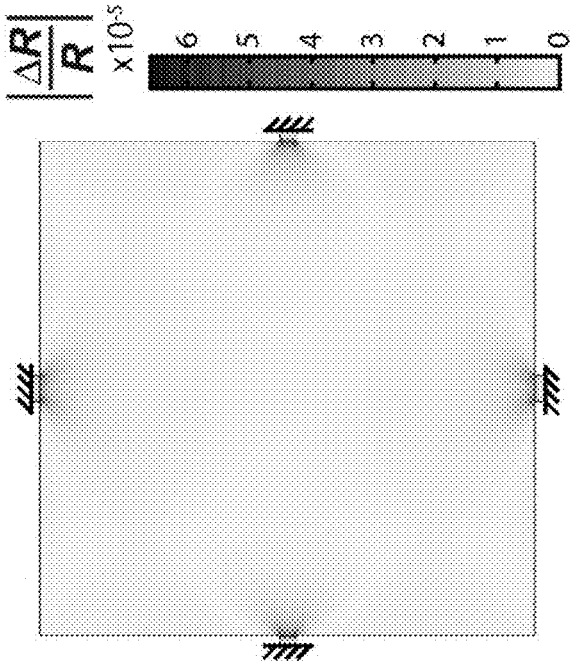
FIG. 9(a) is a diagram illustrating the result of finite element analysis in a case where both surfaces are coated in the MSS as illustrated in FIGS. 7, 8(a) and 8(b)
Figure 9B:
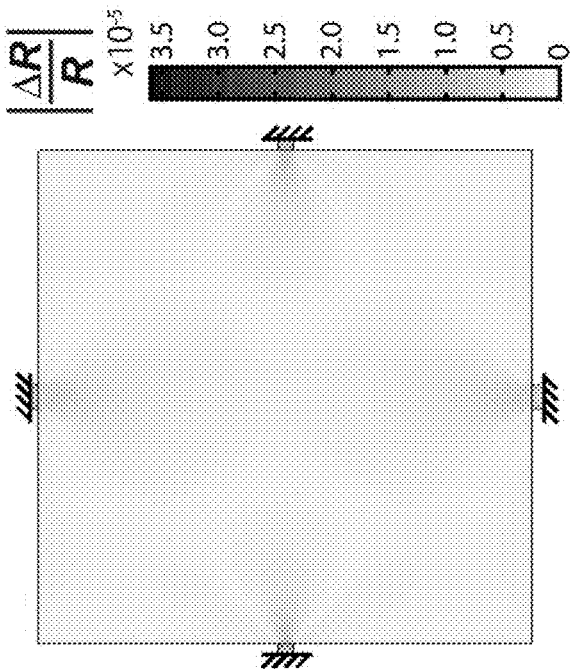
FIG. 9(b) is a diagram illustrating the result of finite element analysis in a case where only a single surface is coated in the MSS as illustrated in FIGS. 7, 8(a) and 8(b).

FIG. 9 illustrates the result of the stress distribution calculated by the finite element method in cases where both surfaces are coated on the silicon membrane portion (FIG. 9(*a*)) and a single surface is coated on the silicon membrane portion (FIG. 9(*b*)), in the MSS structure as illustrated in FIGS. 7 and 8(*b*). Comparing FIG. 9(*a*) and FIG. 9(*b*) (particularly, color strength of the portion indicated by a small rectangle in the center of each side in the square shade of the portion corresponding to the cuboids 73, 75, 77, and 79 in FIG. 7), the stress is concentrated on the portion that is connected to silicon membrane portion in the bulk silicon substrate in a case of the double-side-coated surface (a), whereas in a case of the single-side-coated surface (b), the aforementioned concentrated stress weakens.

In this way, the improved MSS structures as shown in FIGS. 7, 8, and the like exhibit high sensitivity in a case of the double-side-coated surface unlike the structure in FIG. 4.

INDUSTRIAL APPLICABILITY

According to the invention, since there is provided a surface stress sensor having high sensitivity, of which both faces are coated by a practically useful receptor layer, it is possible to greatly contribute to a practical application of fields in relation to such a nanomechanical sensor.

The invention claimed is:

1. A double-side-coated surface stress sensor comprising:
a sensing membrane structure portion where at least two ends opposite each other are fixed on a mounting portion;
a receptor layer that coats both surfaces of the sensing membrane structure portion; and
an element detecting a stress, which is provided in the vicinity of at least one of the fixed two ends, opposite each other, of the sensing membrane structure portion or at least one of two fixed ends, opposite each other, of the mounting portion,
wherein a detection output is obtained from the element based on the stress which is applied onto the receptor layer coating both surfaces of the sensing membrane structure portion.

2. The double-side-coated surface stress sensor according to claim 1,
wherein the stress applied onto the receptor layer is a stress generated by expanding and contracting the receptor layer.

3. The double-side-coated surface stress sensor according to claim 2,
wherein the expansion and contraction of the receptor layer is generated by adsorbing a substance to be detected onto the receptor layer.

4. The double-side-coated surface stress sensor according to claim 1,
wherein the stress applied onto the receptor layer is a stress excited by a magnetic field or radiation.

5. The double-side-coated surface stress sensor according to claim 1,
wherein the element includes a piezoresistance.

6. The double-side-coated surface stress sensor according to claim 1,
wherein the sensing membrane structure portion or the mounting portion is formed of a single crystal silicon, and
wherein the element is a region that is obtained by doping an impurity expressing an effect of the piezoresistance on a surface provided in the vicinity of at least one of the fixed two ends, opposite each other, of the sensing membrane structure portion or at least one of the fixed two ends, opposite each other, of the mounting portion.

7. The double-side-coated surface stress sensor according to claim 6,
wherein the doping of the impurity is performed by implanting or diffusing ions.

8. The double-side-coated surface stress sensor according to claim 1,
wherein a portion where the element is provided in the end is a narrow portion formed into a small-width shape.

9. The double-side-coated surface stress sensor according to claim 8,
wherein the ends of the sensing membrane structure portion are a first end and a second end on an axis in a longitudinal direction of the sensing membrane structure portion,
wherein the narrow portion is provided in at least one of the first end and the second end, and
wherein the element is provided in the narrow portion.

10. The double-side-coated surface stress sensor according to claim 1,
wherein the ends fixed to the mounting portion include
a first end and a second end on a first axis on a surface of the sensing membrane structure portion, and
a third end and a fourth end on a second axis intersecting the first axis on the surface of the sensing membrane structure portion.

11. The double-side-coated surface stress sensor according to claim 10, wherein the first axis and the second axis substantially intersect each other on the sensing membrane structure portion, and wherein the sensing membrane structure portion is rotationally symmetric around an intersection point of the first axis and the second axis.

12. The double-side-coated surface stress sensor according to claim 10, wherein a narrow portion formed into a small width shape is provided in each of the first to fourth ends, and wherein the element is provided in each narrow portion which is provided in the first to fourth ends.

13. The double-side-coated surface stress sensor according to claim 10, wherein the element detecting the stress is provided in the vicinity of each of the first to fourth ends in the mounting portion.

14. The double-side-coated surface stress sensor according to claim 1, wherein the receptor layer is formed of any one of a silane or Au-thiol self-assembled monolayer, a polymer, and an evaporated film.

15. The double-side-coated surface stress sensor according to claim 14, wherein the receptor layer includes at least one selected from the group consisting of APTES, AEAPS, OTS, alkanethiol, MHA, single-strand oligo-DNA introducing a thiol group at the end, PSS, PMMA, and PEI.

16. The double-side-coated surface stress sensor according to claim 1, wherein the receptor layer is the surface of the sensing membrane structure portion.

* * * * *